US006313279B1

United States Patent
Burnett et al.

(10) Patent No.: US 6,313,279 B1
(45) Date of Patent: Nov. 6, 2001

(54) HUMAN GLUTAMATE RECEPTOR AND RELATED DNA COMPOUNDS

(75) Inventors: J. Paul Burnett; Nancy G. Mayne; Robert L. Sharp; Yvonne M. Snyder, all of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 08/172,332

(22) Filed: Dec. 22, 1993

Related U.S. Application Data

(62) Division of application No. 07/879,688, filed on May 1, 1992, now abandoned.

(51) Int. Cl.[7] .......................... C12N 15/12; C07K 14/705
(52) U.S. Cl. ................. 536/23.5; 435/320.1; 435/252.3; 435/325; 435/440
(58) Field of Search ................................. 536/23.1, 23.5, 536/24.3, 24.31, 24.33; 435/6, 240.2, 172.3, 252.3, 252.33, 320.1, 325, 440; 935/11, 27, 34, 50, 70, 72, 73, 77, 78

(56) References Cited

FOREIGN PATENT DOCUMENTS

WO/91/06648    5/1991   (WO) .

OTHER PUBLICATIONS

Potier Direct Sequence Submission to the EMBL/GenBank Library on Mar. 19, 1991 Locus #HSGLURI.*
S.L. Berger et al. "Guide to Molecular Cloning" Meth. in Enzymol. vol. 1652, pp. 393–399, 415–423, 432–449, 663–704 (1987).*
Puckett, et al., "Molecular cloning and chromosomal localization of one of the human glutamate receptor genes", *Proceedings of the National Academy of Sciences*, 88 (17), 7557–7561 (1991).
Sun, et al., "Molecular cloning, chromosomal mapping, and functional expression of human brain glutamate receptors", *Proceedings of the National Academy of Sciences*, 89 (4), 1443–1447 (1992).
Unwin, "The Structure of Ion Channels in Membranes of Excitable Cells", *Neuron*, 3, 665–676 (1989).
Keinaenen, et al., "A family of AMPA–selective glutamate receptors", *Science*, 249, 556–560 (1990).
Sakimura, et al., "Functional expression of a member of the glutamate receptor family", *Neuron*, 8, 257–265 (1992).
Werner, et al., "Cloning of a putative high–affinity kainate receptor expressed predominantly in hippocampal CA3 cells", *Nature*, 351, 742–744 (1991).
Bettler, et al., "Cloning of a Putative Glutamate Receptor: A Low Affinity Kainate–Binding Subunit", *Neuron*, 8, 257–265 (1992).
Boulter, et al., "Molecular Cloning and Functional Expression of Glutamate Receptor Subunit Genes", *Science*, 249, 1033–1037 (1990).
Hollmann, et al., "Cloning by functional expression of a member of the glutamate receptor family", *Nature*, 342, 643–648 (1989).

* cited by examiner

Primary Examiner—Rebecca E. Prouty
(74) Attorney, Agent, or Firm—Alexander Wilson; Paul J. Gaylo

(57) ABSTRACT

The present invention provides a human glutamate receptor and related DNA compounds useful not only in assays for potential pharmaceuticals but also in methods for molecular biology techniques.

1 Claim, No Drawings

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 906 amino acids
      (B) TYPE: amino acid
      (D) TOPOLOGY: linear (ii) MOLECULE TYPE: protein (xi) SEQUENCE DESCRIPTION: SEQ ID NO:1:

```
Met Gln His Ile Phe Ala Phe Phe Cys Thr Gly Phe Leu Gly Ala Val
 1               5                  10                  15

Val Gly Ala Asn Phe Pro Asn Asn Ile Gln Ile Gly Gly Leu Phe Pro
                20                  25                  30

Asn Gln Gln Ser Gln Glu His Ala Ala Phe Arg Phe Ala Leu Ser Gln
            35                  40                  45

Leu Thr Glu Pro Pro Lys Leu Leu Pro Gln Ile Asp Ile Val Asn Ile
        50                  55                  60
```

```
Ser Asp Ser Phe Glu Met Thr Tyr Arg Phe Cys Ser Gln Phe Ser Lys
 65                  70                  75                  80

Gly Val Tyr Ala Ile Phe Gly Phe Tyr Glu Arg Arg Thr Val Asn Met
                 85                  90                  95

Leu Thr Ser Phe Cys Gly Ala Leu His Val Cys Phe Ile Thr Pro Ser
                100                 105                 110

Phe Pro Val Asp Thr Ser Asn Gln Phe Val Leu Gln Leu Arg Pro Glu
            115                 120                 125

Leu Gln Asp Ala Leu Ile Ser Ile Ile Asp His Tyr Lys Trp Gln Lys
        130                 135                 140

Phe Val Tyr Ile Tyr Asp Ala Asp Arg Gly Leu Ser Val Leu Gln Lys
145                 150                 155                 160

Val Leu Asp Thr Ala Ala Glu Lys Asn Trp Gln Val Thr Ala Val Asn
                165                 170                 175

Ile Leu Thr Thr Thr Glu Glu Gly Tyr Arg Met Leu Phe Gln Asp Leu
                180                 185                 190

Glu Lys Lys Lys Glu Arg Leu Val Val Val Asp Cys Glu Ser Glu Arg
            195                 200                 205

Leu Asn Ala Ile Leu Gly Gln Ile Ile Lys Leu Glu Lys Asn Gly Ile
        210                 215                 220

Gly Tyr His Tyr Ile Leu Ala Asn Leu Gly Phe Met Asp Ile Asp Leu
225                 230                 235                 240

Asn Lys Phe Lys Glu Ser Gly Ala Asn Val Thr Gly Phe Gln Leu Val
                245                 250                 255

Asn Tyr Thr Asp Thr Ile Pro Ala Lys Ile Met Gln Gln Trp Lys Asn
                260                 265                 270

Ser Asp Ala Arg Asp His Thr Arg Val Asp Trp Lys Arg Pro Lys Tyr
            275                 280                 285

Thr Ser Ala Leu Thr Tyr Asp Gly Val Lys Val Met Ala Glu Ala Phe
        290                 295                 300

Gln Ser Leu Arg Arg Gln Arg Ile Asp Ile Ser Arg Arg Gly Asn Ala
305                 310                 315                 320

Gly Asp Cys Leu Ala Asn Pro Ala Val Pro Trp Gly Gln Gly Ile Asp
                325                 330                 335

Ile Gln Arg Ala Leu Gln Gln Val Arg Phe Glu Gly Leu Thr Gly Asn
                340                 345                 350

Val Gln Phe Asn Glu Lys Gly Arg Arg Thr Asn Tyr Thr Leu His Val
            355                 360                 365

Ile Glu Met Lys His Asp Gly Ile Arg Lys Ile Gly Tyr Trp Asn Glu
        370                 375                 380

Asp Asp Lys Phe Val Pro Ala Ala Thr Asp Ala Gln Ala Gly Gly Asp
385                 390                 395                 400

Asn Ser Ser Val Gln Asn Arg Thr Tyr Ile Val Thr Thr Ile Leu Glu
                405                 410                 415

Asp Pro Tyr Val Met Leu Lys Lys Asn Ala Asn Gln Phe Glu Gly Asn
                420                 425                 430

Asp Arg Tyr Glu Gly Tyr Cys Val Glu Leu Ala Ala Glu Ile Ala Lys
            435                 440                 445

His Val Gly Tyr Ser Tyr Arg Leu Glu Ile Val Ser Asp Gly Lys Tyr
        450                 455                 460

Gly Ala Arg Asp Pro Asp Thr Lys Ala Trp Asn Gly Met Val Gly Glu
465                 470                 475                 480
```

```
Leu Val Tyr Gly Arg Ala Asp Val Ala Val Pro Leu Thr Ile Thr
            485                 490                 495

Leu Val Arg Glu Glu Val Ile Asp Phe Ser Lys Pro Phe Met Ser Leu
            500                 505                 510

Gly Ile Ser Ile Met Ile Lys Lys Pro Gln Lys Ser Lys Pro Gly Val
            515                 520                 525

Phe Ser Phe Leu Asp Pro Leu Ala Tyr Glu Ile Trp Met Cys Ile Val
            530                 535                 540

Phe Ala Tyr Ile Gly Val Ser Val Val Leu Phe Leu Val Ser Arg Phe
545                 550                 555                 560

Ser Pro Tyr Glu Trp His Ser Glu Glu Phe Glu Glu Gly Arg Asp Gln
            565                 570                 575

Thr Thr Ser Asp Gln Ser Asn Glu Phe Gly Ile Phe Asn Ser Leu Trp
            580                 585                 590

Phe Ser Leu Gly Ala Phe Met Gln Gln Gly Cys Asp Ile Ser Pro Arg
            595                 600                 605

Ser Leu Ser Gly Arg Ile Val Gly Gly Val Trp Trp Phe Phe Thr Leu
            610                 615                 620

Ile Ile Ile Ser Ser Tyr Thr Ala Asn Leu Ala Ala Phe Leu Thr Val
625                 630                 635                 640

Glu Arg Met Val Ser Pro Ile Glu Ser Ala Glu Asp Leu Ala Lys Gln
            645                 650                 655

Thr Glu Ile Ala Tyr Gly Thr Leu Glu Ala Gly Ser Thr Lys Glu Phe
            660                 665                 670

Phe Arg Arg Ser Lys Ile Ala Val Phe Glu Lys Met Trp Thr Tyr Met
            675                 680                 685

Lys Ser Ala Glu Pro Ser Val Phe Val Arg Thr Thr Glu Glu Gly Met
            690                 695                 700

Ile Arg Val Arg Lys Ser Lys Gly Lys Tyr Ala Tyr Leu Leu Glu Ser
705                 710                 715                 720

Thr Met Asn Glu Tyr Ile Glu Gln Arg Lys Pro Cys Asp Thr Met Lys
            725                 730                 735

Val Gly Gly Asn Leu Asp Ser Lys Gly Tyr Gly Ile Ala Thr Pro Lys
            740                 745                 750

Gly Ser Ala Leu Arg Asn Pro Val Asn Leu Ala Val Leu Lys Leu Asn
            755                 760                 765

Glu Gln Gly Leu Leu Asp Lys Leu Lys Asn Lys Trp Trp Tyr Asp Lys
            770                 775                 780

Gly Glu Cys Gly Ser Gly Gly Gly Asp Ser Lys Asp Lys Thr Ser Ala
785                 790                 795                 800

Leu Ser Leu Ser Asn Val Ala Gly Val Phe Tyr Ile Leu Ile Gly Gly
            805                 810                 815

Leu Gly Leu Ala Met Leu Val Ala Leu Ile Glu Phe Cys Tyr Lys Ser
            820                 825                 830

Arg Ser Glu Ser Lys Arg Met Lys Gly Phe Cys Leu Ile Pro Gln Gln
            835                 840                 845

Ser Ile Asn Glu Ala Ile Arg Thr Ser Thr Leu Pro Arg Asn Ser Gly
            850                 855                 860

Ala Gly Ala Ser Ser Gly Gly Ser Gly Glu Asn Gly Arg Val Val Ser
865                 870                 875                 880
```

```
His Asp Phe Pro Lys Ser Met Gln Ser Ile Pro Cys Met Ser His Ser
            885                 890                 895

Ser Gly Met Pro Leu Gly Ala Thr Gly Leu
            900                 905

(2) INFORMATION FOR SEQ ID NO:2:

(i) SEQUENCE CHARACTERISTICS:
        (A) LENGTH: 2718 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..2718

(xi) SEQUENCE DESCRIPTION: SEQ ID NO:2:

ATG CAG CAC ATT TTT GCC TTC TTC TGC ACC GGT TTC CTA GGC GCG GTA      48
Met Gln His Ile Phe Ala Phe Phe Cys Thr Gly Phe Leu Gly Ala Val
 1               5                  10                  15

GTA GGT GCC AAT TTC CCC AAC AAT ATC CAG ATC GGG GGA TTA TTT CCA      96
Val Gly Ala Asn Phe Pro Asn Asn Ile Gln Ile Gly Gly Leu Phe Pro
                20                  25                  30

AAC CAG CAG TCA CAG GAA CAT GCT GCT TTT AGA TTT GCT TTG TCG CAA     144
Asn Gln Gln Ser Gln Glu His Ala Ala Phe Arg Phe Ala Leu Ser Gln
            35                  40                  45

CTC ACA GAG CCC CCG AAG CTG CTC CCC CAG ATT GAT ATT GTG AAC ATC     192
Leu Thr Glu Pro Pro Lys Leu Leu Pro Gln Ile Asp Ile Val Asn Ile
        50                  55                  60

AGC GAC AGC TTT GAG ATG ACC TAT AGA TTC TGT TCC CAG TTC TCC AAA     240
Ser Asp Ser Phe Glu Met Thr Tyr Arg Phe Cys Ser Gln Phe Ser Lys
 65                  70                  75                  80

GGA GTC TAT GCC ATC TTT GGG TTT TAT GAA CGT AGG ACT GTC AAC ATG     288
Gly Val Tyr Ala Ile Phe Gly Phe Tyr Glu Arg Arg Thr Val Asn Met
                85                  90                  95

CTG ACC TCC TTT TGT GGG GCC CTC CAC GTC TGC TTC ATT ACG CCG AGC     336
Leu Thr Ser Phe Cys Gly Ala Leu His Val Cys Phe Ile Thr Pro Ser
                100                 105                 110

TTT CCC GTT GAT ACA TCC AAT CAG TTT GTC CTT CAG CTG CGC CCT GAA     384
Phe Pro Val Asp Thr Ser Asn Gln Phe Val Leu Gln Leu Arg Pro Glu
            115                 120                 125

CTG CAG GAT GCC CTC ATC AGC ATC ATT GAC CAT TAC AAG TGG CAG AAA     432
Leu Gln Asp Ala Leu Ile Ser Ile Ile Asp His Tyr Lys Trp Gln Lys
        130                 135                 140

TTT GTC TAC ATT TAT GAT GCC GAC CGG GGC TTA TCC GTC CTG CAG AAA     480
Phe Val Tyr Ile Tyr Asp Ala Asp Arg Gly Leu Ser Val Leu Gln Lys
145                 150                 155                 160

GTC CTG GAT ACA GCT GCT GAG AAG AAC TGG CAG GTG ACA GCA GTC AAC     528
Val Leu Asp Thr Ala Ala Glu Lys Asn Trp Gln Val Thr Ala Val Asn
                165                 170                 175

ATT TTG ACA ACC ACA GAG GAG GGA TAC CGG ATG CTC TTT CAG GAC CTG     576
Ile Leu Thr Thr Thr Glu Glu Gly Tyr Arg Met Leu Phe Gln Asp Leu
                180                 185                 190

GAG AAG AAA AAG GAG CGG CTG GTG GTG GTG GAC TGT GAA TCA GAA CGC     624
Glu Lys Lys Lys Glu Arg Leu Val Val Val Asp Cys Glu Ser Glu Arg
            195                 200                 205

CTC AAT GCT ATC TTG GGC CAG ATT ATA AAG CTA GAG AAG AAT GGC ATC     672
Leu Asn Ala Ile Leu Gly Gln Ile Ile Lys Leu Glu Lys Asn Gly Ile
        210                 215                 220
```

```
GGC TAC CAC TAC ATT CTT GCA AAT CTG GGC TTC ATG GAC ATT GAC TTA        720
Gly Tyr His Tyr Ile Leu Ala Asn Leu Gly Phe Met Asp Ile Asp Leu
225                 230                 235                 240

AAC AAA TTC AAG GAG AGT GGC GCC AAT GTG ACA GGT TTC CAG CTG GTG        768
Asn Lys Phe Lys Glu Ser Gly Ala Asn Val Thr Gly Phe Gln Leu Val
                245                 250                 255

AAC TAC ACA GAC ACT ATT CCG GCC AAG ATC ATG CAG CAG TGG AAG AAT        816
Asn Tyr Thr Asp Thr Ile Pro Ala Lys Ile Met Gln Gln Trp Lys Asn
            260                 265                 270

AGT GAT GCT CGA GAC CAC ACA CGG GTG GAC TGG AAG AGA CCC AAG TAC        864
Ser Asp Ala Arg Asp His Thr Arg Val Asp Trp Lys Arg Pro Lys Tyr
        275                 280                 285

ACC TCT GCG CTC ACC TAC GAT GGG GTG AAG GTG ATG GCT GAG GCT TTC        912
Thr Ser Ala Leu Thr Tyr Asp Gly Val Lys Val Met Ala Glu Ala Phe
    290                 295                 300

CAG AGC CTG CGG AGG CAG AGA ATT GAT ATA TCT CGC CGG GGG AAT GCT        960
Gln Ser Leu Arg Arg Gln Arg Ile Asp Ile Ser Arg Arg Gly Asn Ala
305                 310                 315                 320

GGG GAT TGT CTG GCT AAC CCA GCT GTT CCC TGG GGC CAA GGG ATC GAC       1008
Gly Asp Cys Leu Ala Asn Pro Ala Val Pro Trp Gly Gln Gly Ile Asp
                325                 330                 335

ATC CAG AGA GCT CTG CAG CAG GTG CGA TTT GAA GGT TTA ACA GGA AAC       1056
Ile Gln Arg Ala Leu Gln Gln Val Arg Phe Glu Gly Leu Thr Gly Asn
            340                 345                 350

GTG CAG TTT AAT GAG AAA GGA CGC CGG ACC AAC TAC ACG CTC CAC GTG       1104
Val Gln Phe Asn Glu Lys Gly Arg Arg Thr Asn Tyr Thr Leu His Val
        355                 360                 365

ATT GAA ATG AAA CAT GAC GGC ATC CGA AAG ATT GGT TAC TGG AAT GAA       1152
Ile Glu Met Lys His Asp Gly Ile Arg Lys Ile Gly Tyr Trp Asn Glu
    370                 375                 380

GAT GAT AAG TTT GTC CCT GCA GCC ACC GAT GCC CAA GCT GGG GGC GAT       1200
Asp Asp Lys Phe Val Pro Ala Ala Thr Asp Ala Gln Ala Gly Gly Asp
385                 390                 395                 400

AAT TCA AGT GTT CAG AAC AGA ACA TAC ATC GTC ACA ACA ATC CTA GAA       1248
Asn Ser Ser Val Gln Asn Arg Thr Tyr Ile Val Thr Thr Ile Leu Glu
                405                 410                 415

GAT CCT TAT GTG ATG CTC AAG AAG AAC GCC AAT CAG TTT GAG GGC AAT       1296
Asp Pro Tyr Val Met Leu Lys Lys Asn Ala Asn Gln Phe Glu Gly Asn
            420                 425                 430

GAC CGT TAC GAG GGC TAC TGT GTA GAG CTG GCG GCA GAG ATT GCC AAG       1344
Asp Arg Tyr Glu Gly Tyr Cys Val Glu Leu Ala Ala Glu Ile Ala Lys
        435                 440                 445

CAC GTG GGC TAC TCC TAC CGT CTG GAG ATT GTC AGT GAT GGA AAA TAC       1392
His Val Gly Tyr Ser Tyr Arg Leu Glu Ile Val Ser Asp Gly Lys Tyr
    450                 455                 460

GGA GCC CGA GAC CCT GAC ACG AAG GCC TGG AAT GGC ATG GTG GGA GAG       1440
Gly Ala Arg Asp Pro Asp Thr Lys Ala Trp Asn Gly Met Val Gly Glu
465                 470                 475                 480

CTG GTC TAT GGA AGA GCA GAT GTG GCT GTG GCT CCC TTA ACT ATC ACT       1488
Leu Val Tyr Gly Arg Ala Asp Val Ala Val Ala Pro Leu Thr Ile Thr
                485                 490                 495

TTG GTC CGG GAA GAA GTT ATA GAT TTC TCC AAA CCA TTT ATG AGT TTG       1536
Leu Val Arg Glu Glu Val Ile Asp Phe Ser Lys Pro Phe Met Ser Leu
            500                 505                 510

GGG ATC TCC ATC ATG ATT AAA AAA CCA CAG AAA TCC AAG CCG GGT GTC       1584
Gly Ile Ser Ile Met Ile Lys Lys Pro Gln Lys Ser Lys Pro Gly Val
        515                 520                 525

TTC TCC TTC CTT GAT CCT TTG GCT TAT GAG ATT TGG ATG TGC ATT GTT       1632
Phe Ser Phe Leu Asp Pro Leu Ala Tyr Glu Ile Trp Met Cys Ile Val
    530                 535                 540
```

```
TTT GCC TAC ATT GGA GTG AGT GTT GTC CTC TTC CTG GTC AGC CGC TTC      1680
Phe Ala Tyr Ile Gly Val Ser Val Val Leu Phe Leu Val Ser Arg Phe
545                 550                 555                 560

AGT CCC TAT GAA TGG CAC AGT GAA GAG TTT GAG GAA GGA CGG GAC CAG      1728
Ser Pro Tyr Glu Trp His Ser Glu Glu Phe Glu Glu Gly Arg Asp Gln
                565                 570                 575

ACA ACC AGT GAC CAG TCC AAT GAG TTT GGG ATA TTC AAC AGT TTG TGG      1776
Thr Thr Ser Asp Gln Ser Asn Glu Phe Gly Ile Phe Asn Ser Leu Trp
            580                 585                 590

TTC TCC CTG GGA GCC TTC ATG CAG CAA GGA TGT GAC ATT TCT CCC AGG      1824
Phe Ser Leu Gly Ala Phe Met Gln Gln Gly Cys Asp Ile Ser Pro Arg
        595                 600                 605

TCC CTG TCT GGT CGC ATC GTT GGT GGC GTC TGG TGG TTC TTC ACC TTA      1872
Ser Leu Ser Gly Arg Ile Val Gly Gly Val Trp Trp Phe Phe Thr Leu
    610                 615                 620

ATC ATC ATC TCC TCA TAT ACA GCC AAT CTG GCC GCC TTC CTG ACC GTG      1920
Ile Ile Ile Ser Ser Tyr Thr Ala Asn Leu Ala Ala Phe Leu Thr Val
625                 630                 635                 640

GAG AGG ATG GTG TCT CCC ATT GAG AGT GCA GAG GAC CTA GCG AAG CAG      1968
Glu Arg Met Val Ser Pro Ile Glu Ser Ala Glu Asp Leu Ala Lys Gln
                645                 650                 655

ACA GAA ATT GCC TAC GGG ACG CTG GAA GCA GGA TCT ACT AAG GAG TTC      2016
Thr Glu Ile Ala Tyr Gly Thr Leu Glu Ala Gly Ser Thr Lys Glu Phe
            660                 665                 670

TTC AGG AGG TCT AAA ATT GCT GTG TTT GAG AAG ATG TGG ACA TAC ATG      2064
Phe Arg Arg Ser Lys Ile Ala Val Phe Glu Lys Met Trp Thr Tyr Met
        675                 680                 685

AAG TCA GCA GAG CCA TCA GTT TTT GTG CGG ACC ACA GAG GAG GGG ATG      2112
Lys Ser Ala Glu Pro Ser Val Phe Val Arg Thr Thr Glu Glu Gly Met
    690                 695                 700

ATT CGA GTG AGG AAA TCC AAA GGC AAA TAT GCC TAC CTC CTG GAG TCC      2160
Ile Arg Val Arg Lys Ser Lys Gly Lys Tyr Ala Tyr Leu Leu Glu Ser
705                 710                 715                 720

ACC ATG AAT GAG TAC ATT GAG CAG CGG AAA CCC TGT GAC ACC ATG AAG      2208
Thr Met Asn Glu Tyr Ile Glu Gln Arg Lys Pro Cys Asp Thr Met Lys
                725                 730                 735

GTG GGA GGT AAC TTG GAT TCC AAA GGC TAT GGC ATT GCA ACA CCC AAG      2256
Val Gly Gly Asn Leu Asp Ser Lys Gly Tyr Gly Ile Ala Thr Pro Lys
            740                 745                 750

GGG TCT GCC CTG AGA AAT CCA GTA AAC CTG GCA GTG TTA AAA CTG AAC      2304
Gly Ser Ala Leu Arg Asn Pro Val Asn Leu Ala Val Leu Lys Leu Asn
        755                 760                 765

GAG CAG GGG CTT TTG GAC AAA TTG AAA AAC AAA TGG TGG TAC GAC AAG      2352
Glu Gln Gly Leu Leu Asp Lys Leu Lys Asn Lys Trp Trp Tyr Asp Lys
    770                 775                 780

GGC GAG TGC GGC AGC GGG GGA GGT GAT TCC AAG GAC AAG ACA AGC GCT      2400
Gly Glu Cys Gly Ser Gly Gly Gly Asp Ser Lys Asp Lys Thr Ser Ala
785                 790                 795                 800

CTG AGC CTC AGC AAT GTG GCA GGC GTG TTC TAC ATC CTG ATC GGA GGA      2448
Leu Ser Leu Ser Asn Val Ala Gly Val Phe Tyr Ile Leu Ile Gly Gly
                805                 810                 815

CTT GGA CTA GCC ATG CTG GTT GCC TTA ATC GAG TTC TGC TAC AAA TCC      2496
Leu Gly Leu Ala Met Leu Val Ala Leu Ile Glu Phe Cys Tyr Lys Ser
            820                 825                 830

CGT AGT GAA TCC AAG CGG ATG AAG GGT TTT TGT TTG ATC CCA CAG CAA      2544
Arg Ser Glu Ser Lys Arg Met Lys Gly Phe Cys Leu Ile Pro Gln Gln
        835                 840                 845

TCC ATC AAC GAA GCC ATA CGG ACA TCG ACC CTC CCC CGC AAC AGC GGG      2592
Ser Ile Asn Glu Ala Ile Arg Thr Ser Thr Leu Pro Arg Asn Ser Gly
    850                 855                 860
```

```
GCA GGA GCC AGC AGC GGC GGC AGT GGA GAG AAT GGT CGG GTG GTC AGC        2640
Ala Gly Ala Ser Ser Gly Gly Ser Gly Glu Asn Gly Arg Val Val Ser
865                 870                 875                 880

CAT GAC TTC CCC AAG TCC ATG CAA TCG ATT CCT TGC ATG AGC CAC AGT        2688
His Asp Phe Pro Lys Ser Met Gln Ser Ile Pro Cys Met Ser His Ser
                885                 890                 895

TCA GGG ATG CCC TTG GGA GCC ACG GGA TTG                                2718
Ser Gly Met Pro Leu Gly Ala Thr Gly Leu
            900                 905
```

(2) INFORMATION FOR SEQ ID NO:3:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1..60

(xi) SEQUENCE DESCRIPTION: SEQ ID NO:3:

```
ATG CAG CAC ATT TTT GCC TTC TTC TGC ACC GGT TTC CTA GGC GCG GTA         48
Met Gln His Ile Phe Ala Phe Phe Cys Thr Gly Phe Leu Gly Ala Val
1               5                   10                  15

GTA GGT GCC AAT                                                         60
Val Gly Ala Asn
            20
```

(2) INFORMATION FOR SEQ ID NO:4:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1-60

(xi) SEQUENCE DESCRIPTION: SEQ ID NO:4:

```
                                TTT GCT TTG TCG CAA                     15
                                Phe Ala Leu Ser Gln
                                1               5

CTC ACA GAG CCC CCG AAG CTG CTC CCC CAG ATT GAT ATT GTG AAC             60
Leu Thr Glu Pro Pro Lys Leu Leu Pro Gln Ile Asp Ile Val Asn
                10                  15                  20
```

(2) INFORMATION FOR SEQ ID NO:5:

(i) SEQUENCE CHARACTERISTICS:
        (A) LENGTH: 60 base pairs
        (B) TYPE: nucleic acid
        (C) STRANDEDNESS: both
        (D) TOPOLOGY: linear (ii) MOLECULE TYPE: cDNA (ix) FEATURE:
        (A) NAME/KEY: CDS
        (B) LOCATION: 1-60

(xi) SEQUENCE DESCRIPTION: SEQ ID NO:5:

```
                        CAA TCG ATT CCT TGC ATG AGC CAC AGT         27
                        Gln Ser Ile Pro Cys Met Ser His Ser
                         1               5

TCA GGG ATG CCC TTG GGA GCC ACG GGA TTG TAA                         60
Ser Gly Met Pro Leu Gly Ala Thr Gly Leu
 10                  15
```

HUMAN GLUTAMATE RECEPTOR AND RELATED DNA COMPOUNDS

This application is a division, of application Ser. No. 07/879,688 filed May 1, 1992 now abandoned.

BACKGROUND OF THE INVENTION

In the mammalian central nervous system, L-glutamate serves as a major excitatory neurotransmitter. The interaction of glutamate with its membrane-bound receptors is believed to play a role in many important neuronal processes, including, for example, fast synaptic transmission, synaptic plasticity and long-term potentiation. These processes are fundamental to the maintenance of life and normal human abilities such as learning and memory. Monaghan D. T. et al., 8 Neuron 267 (1992).

Pharmacological characterization of receptors for L-glutamate has led to their classification into two families based on their biological function: the ionotropic receptors which are directly coupled to cation channels in the cell membrane, and the metabotropic receptors which function through coupling to G-proteins. A number of ionotropic receptors have been further characterized on the basis of the relatively specific agonists by which they can be activated. One major group comprises those receptors activated by N-methyl-D-aspartate (NMDA), which appears to have multiple allosteric modulatory sites. The other two groups consist of those receptors activated by kainate and/or amino-3-hydroxy-5-methyl-4-isoxozole propionate (AMPA). Collingridge G. L. et al., 40 Pharmacol. Rev. 143 (1989).

Molecular cloning studies of rodent ionotropic receptors have recently provided some information on the molecular structure of these proteins. The cDNAs for seven different subtypes of the kainate/AMPA group have been characterized. Heinemann S. et al., PCT publication, W091/06648 (1991), Keinanen K. et al., 249 Science 556 (1990), Sakimura K. et al., 272 FEBS Lett. 73 (1990), Werner P. et al., 341 Nature 742 (1991), Bettler B. et al., 8 Neuron 257 (1992). Splice variants, referred to as "flip" and "flop", of some of these have been characterized as well. Sommer B. et al., 249 Science 1580 (1990). In addition, one member of the NMDA group has been cloned. Moriyoshi, K. et al., 354 Nature 31 (1991). An NNDA-related protein has also been reported. Kumar K. N. et al., 354 Nature 70 (1991). These proteins share varying degrees of homology with one another and are therefore believed to represent a gene superfamily. Based on analogy with other better characterized ion channel receptors, glutamate ionotropic receptors are expected to exist in vivo within the cell membrane as multisubunit assemblies of these subunits. Unwin N., 3 Neuron 665 (1989).

Moreover, at least two human glutamate receptors have been reported as cloned. The reported human receptors differ slightly from the present invention. Puckett C. et al., 88 Proc. Nat. Acad. Sci. 7557 (1991) and Sun W. et al., 89 Proc. Nat. Acad. Sci. 1443 (1992). The glutamate receptor cloned by Puckett et al. was named GluHI and was later identified to be the "flip" version of this particular receptor. The Sun W. et al. reference refers to the glutamate receptor they cloned as the HBGR1 receptor and explains that HBGR1 is presumed the "flop" version of GluHI. Sun et al. also discloses a partial clone of HBGR2, or GluH2.

In addition to its role in normal human physiology, interaction of L-glutamate with its receptors is believed to play a key role in many neurological disorders such as stroke, epilepsy and head trauma, as well as neurodegenerative processes such as Alzheimer's disease. Olney R. W., 17 Drug Dev. Resa., 299 (1999). For this reason, understanding the molecular structure of human L-glutamate receptors will be important for understanding these disease processes as well as furthering the search for effective therapeutic agents. Up to the present, the search for therapeutic agents which will selectively bind and modulate the function of human glutamate receptors has been hampered by the unavailability of homogeneous sources of receptors to use for screens and tests of potential drug candidate compounds. The brain tissues commonly used by pharmacologists presently are derived from experimental animals (non-human) and furthermore contain mixtures of various types of glutamate receptors.

In searching for drugs for human therapy it is desirable to use receptors that are more analogous to those in the intact human brain than are the rodent receptors employed to date. The current invention provides a human receptor which can be used to search for drugs which modulate these receptors.

SUMMARY OF THE INVENTION

The present invention provides amino acid compounds which comprise the isolated amino acid sequence SEQ ID NO:1. In particular, the amino acid compound which is SEQ ID NO: 1 is preferred.

The invention also provides nucleic acid compounds which comprise an isolated nucleic acid sequence which encodes the amino acid compounds provided. Particularly, nucleic acid compounds which are DNA are preferred. Most preferred is the DNA compound SEQ ID NO:2. However, also preferred are those nucleic acid compounds which are sense mRNA.

Also provided by the present invention are recombinant nucleic acid vectors comprising the nucleic acids which encode SEQ ID NO:1. Preferred nucleic acid vectors are those which are DNA. Most preferred are recombinant DNA vectors which comprise SEQ ID NO:2. The recombinant DNA vector most preferred is plasmid pRS103.

Moreover, recombinant DNA vectors of the present invention preferably comprise a promoter positioned to drive expression of said isolated DNA sequence. A preferred recombinant DNA expression vector is one wherein the promoter functions in mammalian cells. A more preferred recombinant DNA expression vector is one wherein the promoter functions in COS-7 cells. Most preferred COS-7 cell DNA expression vectors further comprise SEQ ID NO:2.

Restriction fragments of the preferred vector are also provided. Particularly, the 4.2 kb (kilobase) EcoRI/Kpn1 and the 2.8 kb EcoRI/ClaI restriction fragment of pRS103 are provided.

The present invention also provides probes and primers useful for molecular biology techniques. Compounds which encode for SEQ ID NO:1 or a part thereof and which are at least 17 base pairs in length are provided. Preferably, the 17 base pair or more compound is DNA. Most preferred for this use are the DNA compounds which are SEQ ID NO:3, SEQ ID NO:4 and SEQ ID NO:5.

Further, this invention provides cells in which the nucleic acid compounds of the invention may be harbored. Oocytes wherein nucleic acid compounds of the invention express functional HSGluR1 receptor are provided. Moreover, oocytes wherein nucleic acids of the present invention express functional HSGluR1 receptor and wherein functional GluR2 receptor is also expressed is provided. Oocytes wherein nucleic acids of the present invention express functional HSGluR1 receptor and wherein functional GluR2 receptor is co-expressed, and wherein functional GluR3 receptor is additionally expressed is also provided. An oocyte wherein DNA expresses functional HSGluR1 receptor is preferred. Most preferred is an oocyte wherein sense mRNA expresses functional HSGluR1 receptor.

Other host cells provided by the present invention include those which are transfected with a nucleic acid compound which encodes SEQ ID NO:1. Preferred cells include host cells transfected with a recombinant DNA vector. Preferred transfected host cells which encodes SEQ ID NO:1 are *E. coli* cells. The most preferred *E. coli* host cell is *E. coli*/pRS103.

Host cells which are transfected with a DNA vector which further comprise a promoter positioned to drive expression of functional HSGluR1 receptor are also provided. Preferably, the DNA vector comprises SEQ ID NO:2. Preferred host cells for expression of functional HSGluR1 are mammalian cells. Preferred mammalian cells for expression of functional HSGluR1 are COS-7 cells. Specifically, COS-7 cells which have been transfected with a DNA expression vector which expresses a functional HSGluR1 receptor and which further comprise a DNA vector which encodes a functional GluR2 receptor are provided. COS-7 cells which have been transfected with an DNA expression vector which expresses a functional HSGluR1 receptor, and which further comprise a DNA vector which encodes a functional GluR2 receptor, and which further comprise a DNA vector which encodes a functional GluR3 receptor are also provided.

Additionally, the invention provides a method for identifying DNA homologous to a probe of the present invention which comprises contacting test nucleic acid with the probe under hybridizing conditions and identifying DNA that is homologous to the probe. The preferred probes for use in this method are SEQ ID NO:3, SEQ ID NO:4 or SEQ ID NO:5.

Assays utilizing the compounds provided by the present invention are also provided. The assays provided determine whether a substance evokes a glutaminergic response, said assays comprising introducing said substance and a functional compound of SEQ ID NO:1 into an acceptable medium, subsequently monitoring glutaminergic activity by physically detectable means, and thereby identifying those substances which effect a chosen response. Other assays further comprise a functional GluR2 receptor. A preferred assay further comprises both a functional GluR2 receptor and a functional GluR3 receptor.

Preferable, the physically detectable means are competition with radiolabeled glutamate, binding of glutaminergic ligand or generating a detectable ion flow. A preferred assay is the oocyte assay system. A most preferred oocyte assay system utilizes sense mRNA.

The invention also provides a method for constructing a recombinant host cell capable of expressing a nucleic acid compound which encodes a compound which comprises SEQ ID NO:1, said method comprising transfecting a host cell with a recombinant DNA vector which comprises said nucleic acid compound. A preferred method utilizes *E. coli* cells as the host cells. A more preferred method further comprises a DNA vector. A most preferred method further comprises a DNA vector which comprises SEQ ID NO:2.

Additionally, a method for expressing a nucleic acid sequence which encodes SEQ ID NO:1 in a recombinant host cell is provided. The method comprises transfecting host cells with nucleic acids of the present invention and culturing the transfected host cells under conditions suitable for gene expression. A preferred method utilizes COS-7 cells as the host cells. A more preferred method utilizes both COS-7 cells and a recombinant DNA vector comprising SEQ ID NO:2.

The following section provides a more detailed description of the present invention. For purposes of clarity and as an aid in understanding the invention, as disclosed and claimed herein, the following items are defined below.

All or part of SEQ ID NO:1—at least 6 consecutive amino acid residues or more of SEQ ID NO:1.

Functional compound of SEQ ID NO:1—A compound comprising SEQ ID NO:1 which is capable of generating ion flow, binding glutamate or binding glutaminergic ligand.

HSGluR1 receptor—the amino acid sequence SEQ ID NO:1.

GluR2 receptor—the amino acid sequence commonly associated with the rat ionotropic glutamate receptor 2.

GluR3 receptor—the amino acid sequence commonly associated with the rat ionotropic glutamate receptor 3.

SEQ ID NO:3—this segment is base 1 through 60 of SEQ ID NO:2, counting from the 5' end: ATG CAG CAC ATT TTT GCC TTC TTC TGC ACC GGT TTC CTA GGC GCG GTA GTA GGT GCC AAT.

SEQ ID NO:4—this segment includes bases 130 through 189 of SEQ ID NO: 2, counting from the 5' end: TTT GCT TTG TCG CAA CTC ACA GAG CCC CCG AAG CTG CTC CCC CAG ATT GAT ATT GTG AAC.

SEQ ID NO:5—this segment includes bases 2662 through 2718 of SEQ ID NO:2, with a TAA stop codon added at the 3' end: CAA TCG ATT CCT TGC ATG AGC CAC AGT TCA GGG ATG CCC TTG GGA GCC ACG GGA TTG TAA.

Transfection—any transfer of nucleic acid into a host cell, with or without integration of said nucleic acid into genome of said host cell.

DETAILED DESCRIPTION OF THE INVENTION

The present invention provides an amino acid compound which comprises the isolated amino acid sequence SEQ ID NO:1. The preferred amino acid compound is SEQ ID NO:1, which is the following sequence of amino acids:

Met Gln His Ile Phe Ala Phe Phe Cys Thr Gly Phe Leu Gly Ala Val
Val Gly Ala Asn Phe Pro Asn Asn Ile Gln Ile Gly Gly Leu Phe Pro
Aen Gln Gln Ser Gln Glu His Ala Ala Phe Arg Phe Ala Leu Ser Gln
Leu Thr Glu Pro Pro Lye Leu Leu Pro Gln Ile Asp Ile Val Asn Ile
Ser Asp Ser Phe Glu Met Thr Tyr Arg Phe Cye Ser Gln Phe Ser Lys
Gly Val Tyr Ala Ile Phe Gly Phe Tyr Glu Arg Arg Thr Val Asn Met
Leu Thr Ser Phe Cys Gly Ala Leu His Val Cys Phe Ile Thr Pro Ser
Phe Pro Val Asp Thr Ser Asn Gln Phe Val Leu Gln Leu Arg Pro Glu
Leu Gln Asp Ala Leu Ile Ser Ile Ile Asp His Tyr Lye Trp Gln Lys
Phe Val Tyr Ile Tyr Asp Ala Asp Arg Gly Leu Ser Val Leu Gln Lys
Val Leu Asp Thr Ala Ala Glu Lys Asn Trp Gln Val Thr Ala Val Asn
Ile Leu Thr Thr Thr Glu Glu Gly Tyr Arg Met Leu Phe Gln Asp Leu
Glu Lys Lys Lys Glu Arg Leu Val Val Asp Cys Glu Ser Glu Arg
Leu Asn Ala Ile Leu Gly Gln Ile Ile Lys Leu Glu Lys Asn Gly Ile
Gly Tyr His Tyr Ile Leu Ala Asn Leu Gly Phe Met Asp Ile Asp Leu
Asn Lye Phe Lye Glu Ser Gly Ala Asn Val Thr Gly Phe Gln Leu Val
Asn Tyr Thr Asp Thr Ile Pro Ala Lys Ile Met Gln Gln Trp Lys Asn
Ser Asp Ala Arg Asp His Thr Arg Val Asp Trp Lys Arg Pro Lys Tyr
Thr Ser Ala Leu Thr Tyr Asp Gly Val Lys Val Met Ala Glu Ala Phe
Gln Ser Leu Arg Arg Gln Arg Ile Asp Ile Ser Arg Arg Gly Asn Ala
Gly Asp Cys Leu Ala Asn Pro Ala Val Pro Trp Gly Gln Gly Ile Asp
Ile Gln Arg Ala Leu Gln Gln Val Arg Phe Glu Gly Leu Thr Gly Asn
Val Gln Phe Asn Glu Lys Gly Arg Arg Thr Asn Tyr Thr Leu His Val
Ile Glu Met Lys His Asp Gly Ile Arg Lye Ile Gly Tyr Trp Asn Glu
Asp Asp Lys Phe Val Pro Ala Ala Thr Asp Ala Gln Ala Gly Gly Asp
Asn Ser Ser Val Gln Asn Arg Thr Tyr Ile Val Thr Thr Ile Leu Glu
Asp Pro Tyr Val Met Leu Lys Lys Asn Ala Asn Gln Phe Glu Gly Asn
Asp Arg Tyr Glu Gly Tyr Cys Val Glu Leu Ala Ala Glu Ile Ala Lys
His Val Gly Tyr Ser Tyr Arg Leu Glu Ile Val Ser Asp Gly Lys Tyr
Gly Ala Arg Asp Pro Asp Thr Lys Ala Trp Asn Gly Met Val Gly Glu
Leu Val Tyr Gly Arg Ala Asp Val Ala Val Ala Pro Leu Thr Ile Thr
Leu Val Arg Glu Glu Val Ile Asp Phe Ser Lys Pro Phe Met Ser Leu
Gly Ile Ser Ile Met Ile Lys Lys Pro Gln Lys Ser Lye Pro Gly Val
Phe Ser Phe Leu Aep Pro Leu Ala Tyr Glu Ile Trp Met Cye Ile Val
Phe Ala Tyr Ile Gly Val Ser Val Val Leu Phe Leu Val Ser Arg Phe
Ser Pro Tyr Glu Trp His Ser Glu Glu Phe Glu Glu Gly Arg Asp Gln
Thr Thr Ser Asp Gln Ser Asn Glu Phe Gly Ile Phe Asn Ser Leu Trp
Phe Ser Leu Gly Ala Phe Met Gln Gln Gly Cye Asp Ile Ser Pro Arg
Ser Leu Ser Gly Arg Ile Val Gly Gly Val Trp Trp Phe Phe Thr Leu
Ile Ile Ile Ser Ser Tyr Thr Ala Asn Leu Ala Ala Phe Leu Thr Val

-continued

```
Glu Arg Met Val Ser Pro Ile Glu Ser Ala Glu Asp Leu Ala Lys Gln

Thr Glu Ile Ala Tyr Gly Thr Leu Glu Ala Gly Ser Thr Lye Glu Phe

Phe Arg Arg Ser Lye Ile Ala Val Phe Glu Lye Met Trp Thr Tyr Met

Lye Ser Ala Glu Pro Ser Val Phe Val Arg Thr Thr Glu Glu Gly Met

Ile Arg Val Arg Lys Ser Lys Gly Lys Tyr Ala Tyr Leu Leu Glu Ser

Thr Met Asn Glu Tyr Ile Glu Gln Arg Lys Pro Cys Asp Thr Met Lys

Val Gly Gly Asn Leu Asp Ser Lys Gly Tyr Gly Ile Ala Thr Pro Lys

Gly Ser Ala Leu Arg Asn Pro Val Asn Leu Ala Val Leu Lys Leu Asn

Glu Gln Gly Leu Leu Asp Lys Leu Lys Asn Lys Trp Typ Tyr Asp Lys

Gly Glu Cys Gly Ser Gly Gly Gly Asp Ser Lys Asp Lys Thr Ser Ala

Leu Ser Leu Ser Asn Val Ala Gly Val Phe Tyr Ile Leu Ile Gly Gly

Leu Gly Leu Ala Met Leu Val Ala Leu Ile Glu Phe Cys Tyr Lys Ser

Arg Ser Glu Ser Lys Arg Met Lye Gly Phe Cys Leu Ile Pro Gln Gln

Ser Ile Asn Glu Ala Ile Arg Thr Ser Thr Leu Pro Arg Asn Ser Gly

Ala Gly Ala Ser Ser Gly Gly Ser Gly Glu Aen Gly Arg Val Val Ser

His Asp Phe Pro Lye Ser Met Gln Ser Ile Pro Cys Met Ser His Ser

Ser Gly Met Pro Leu Gly Ala Thr Gly Leu
```

Skilled artisans will recognize that some alterations of SEQ ID NO:1 will fail to change the function of the amino acid compound. For instance, some hydrophobic amino acids may be exchanged for other hydrophobic amino acids. Those altered amino acid compounds which confer substantially the same function in substantially the same manner as the exemplified amino acid compound are also included in the present invention.

Skilled artisans will also recognize that these proteins can be synthesized by a number of different methods. All of the amino acid compounds of the invention can be made by chemical methods well known in the art, including solid phase peptide synthesis or recombinant methods. Both methods are described in U.S. Pat. No. 4,617,149, herein incorporated by reference. Recombinant methods are preferred if a high yield is desired. A general method for the construction of any desired DNA sequence is provided in Brown et al., 68 *Methods in Enzymology* 109 (1979).

Other routes of production are well known to skilled artisans. Expression in eucaryotic cells can be achieved via SEQ ID NO:2. For example, the amino acid compounds can be produced in eucaryotic cells using SV40-derived expression vectors comprising DNA which encodes for SEQ ID NO:1. As is well known in the art, some viruses are also appropriate vectors. For example, the adenoviruses, the papovaviruses, the vaccinia viruses, the herpes viruses, and the baculoviruses as well as vectors derived from these viruses are useful. Such a method is described in U.S. Pat. No. 4,775,624, herein incorporated by reference. Several alternate methods of expression are described in J. Sambrook, E. F. Fritsch & T. Maniatis, *Molecular Cloning: A Laboratory Manual* 16.3–17.44 (1999) and *Methods in Enzymology*, Vol. 185 (1990).

Other embodiments of the present invention are nucleic acid compounds which comprise isolated nucleic acid sequences which encode all or part of SEQ ID NO:1. As skilled artisans will recognize, the amino acid compounds of the invention can be encoded by a multitude of different nucleic acid sequences because most of the amino acids are encoded by more than one nucleic acid triplet. Because these alternate nucleic acid sequences would encode substantially the same amino acid sequence, the present invention further comprises these alternate nucleic acid sequences. Preferably, the nucleic acid compound is DNA or sense mRNA. A most preferred embodiment of a DNA compound encoding the HSGluR1 compound has this sequence:

ATG CAG CAC ATT TTT GCC TTC TTC TGC ACC GGT TTC CTA GGC GCG GTA

GTA GGT GCC AAT TTC CCC AAC AAT ATC CAG ATC GGG GGA TTA TTT CCA

AAC CAG CAG TCA CAG GAA CAT GCT GCT TTT AGA TTT GCT TTG TCG CAA

CTC ACA GAG CCC CCG AAG CTG CTC CCC CAG ATT GAT ATT GTG AAC ATC

AGC GAC AGC TTT GAG ATG ACC TAT AGA TTC TGT TCC CAG TTC TCC AAA

GGA GTC TAT GCC ATC TTT GGG TTT TAT GAA CGT AGG ACT GTC AAC ATG

-continued

```
CTG ACC TCC TTT TGT GGG GCC CTC CAC GTC TGC TTC ATT ACG CCG AGC
TTT CCC GTT GAT ACA TCC AAT CAG TTT GTC CTT CAG CTG CGC CCT GAA
CTG ACC TCC TTT TGT GGG GCC CTC CAC GTC TGC TTC ATT ACG CCG AGC
TTT GTC TAC ATT TAT GAT GCC GAC CGG GGC TTA TCC GTC CTG CAG AAA
GTC CTG GAT ACA GCT GCT GAG AAG AAC TGG CAG GTG ACA GCA GTC AAC
ATT TTG ACA ACC ACA GAG GAG GGA TAC CGG ATG CTC TTT CAG GAC CTG
GAG AAG AAA AAG GAG CGG CTG GTG GTG GTG GAC TGT GAA TCA GAA CGC
CTC AAT GCT ATC TTG GGC CAG ATT ATA AAG CTA GAG AAG AAT GGC ATC
GGC TAC CAC TAC ATT CTT GCA AAT CTG GGC TTC ATG GAC ATT GAC TTA
AAC AAA TTC AAG GAG AGT GGC GCC AAT GTG ACA GGT TTC CAG CTG GTG
AAC TAC ACA GAC ACT ATT CCG GCC AAG ATC ATG CAG CAG TGG AAG AAT
AGT GAT GCT CGA GAC CAC ACA CGG GTG GAC TGG AAG AGA CCC AAG TAC
ACC TCT GCG CTC ACC TAC GAT GGG GTG AAG GTG ATG GCT GAG GCT TTC
CAG AGC CTG CGG AGG CAG AGA ATT GAT ATA TCT CGC CGG GGG AAT GCT
ATC CAG AGA GCT CTG CAG CAG GTG CGA TTT GAA GGT TTA ACA GGA AAC
GTG CAG TTT AAT GAG AAA GGA CGC CGG ACC AAC TAC ACG CTC CAC GTG
ATT GAA ATG AAA CAT GAC GGC ATC CGA AAG ATT GGT TAC TGG AAT GAA
GAT GAT AAG TTT GTC CCT GCA GCC ACC GAT GCC CAA GCT GGG GGC GAT
AAT TCA AGT GTT CAG AAC AGA ACA TAC ATC GTC ACA ACA ATC CTA GAA
GAT CCT TAT GTG ATG CTC AAG AAG AAC GCC AAT CAG TTT GAG GGC AAT
GAC CGT TAC GAG GGC TAC TGT GTA GAG CTG GCG GCA GAG ATT GCC AAG
CAC GTG GGC TAC TCC TAC CGT CTG GAG ATT GTC AGT GAT GGA AAA TAC
GGA GCC CGA GAC CCT GAC ACG AAG GCC TGG AAT GGC ATC GTG GGA GAG
CTG GTC TAT GGA AGA GCA GAT GTG GCT GTG GCT CCC TTA ACT ATC ACT
TTG GTC CGG GAA GAA GTT ATA GAT TTC TCC AAA CCA TTT ATG AGT TTG
GGG ATC TCC ATC ATG ATT AAA AAA CCA CAG AAA TCC AAG CCG GGT GTC
TTC TCC TTC CTT GAT CCT TTG GCT TAT GAG ATT TGG ATG TGC ATT GTT
TTT GCC TAC ATT GGA GTG AGT GTT GTC CTC TTC CTG GTC AGC CGC TTC
AGT CCC TAT GAA TGG CAC AGT GAA GAG TTT GAG GAA GGA CGG GAC CAG
ACA ACC AGT GAC CAG TCC AAT GAG TTT GGG ATA TTC AAC AGT TTG TGG
TTC TCC CTG GGA GCC TTC ATG CAG CAA GGA TGT GAC ATT CTC CCC AGG
TCC CTG TCT GGT CGC ATC GTT GGT GGC GTC TGG TGG TTC TTC ACC TTA
ATC ATC ATC TCC TCA TAT ACA GCC AAT CTG GCC GCC TTC CTG ACC GTG
GAG AGG ATG GTG TCT CCC ATT GAG AGT GCA GAG GAC CTA GCG AAG CAG
ACA GAA ATT GCC TAC GGG ACG CTG GAA GCA GGA TCT ACT AAG GAG TTC
TTC AGG AGG TCT AAA ATT GCT GTG TTT GAG AAG ATG TGG ACA TAC ATG
ATC ATC ATC TCC TCA TAT ACA GCC AAT CTG GCC GCC TTC CTG ACC GTG
GAG AGG ATG GTG TCT CCC ATT GAG AGT GCA GAG GAC CTA GCG AAG CAG
ACC ATG AAT GAG TAC ATT GAG CAG CGG AAA CCC TGT GAC ACC ATG AAG
GTG GGA GGT AAC TTG GAT TCC AAA GGC TAT GGC ATT GCA ACA CCC AAG
```

-continued

```
GGG TCT GCC CTG AGA AAT CCA GTA AAC CTG GCA GTG TTA AAA CTG AAC

CTG AGC CTC AGC AAT GTG GCA GGC GTG TTC TAC ATC CTG ATC GGA GGA

GGC GAG TGC GGC AGC GGG GGA GGT GAT TCC AAG GAC AAG ACA AGC GCT

CTG AGC CTC AGC AAT GTG GCA GGC GTG TTC TAC ATC CTG ATC GGA GGA

CTT GGA CTA GCC ATG CTG GTT GCC TTA ATC GAG TTC TGC TAC AAA TCC

CGT AGT GAA TCC AAG CGG ATG AAG GGT TTT TGT TTG ATC CCA CAG CAA

TCC ATC AAC GAA GCC ATA CGG ACA TCG ACC CTC CCC CGC AAC AGC GGG

GCA GGA GCC AGC AGC GGC GGC AGT GGA GAG AAT GGT CGG GTG GTC AGC

CAT GAC TTC CCC AAG TCC ATG CAA TCG ATT CCT TGC ATG AGC CAC AGT

TCA GGG ATG CCC TTG GGA GCC ACG GGA TTG
```

This is the sequence identified as SEQ ID NO:2.

E. coli/pRS103, which contains a cloning vector comprising SEQ ID NO:2, was deposited and made part of the stock culture collection of the Northern Regional Research Laboratories (NRRL), Agricultural Research Service, U.S. Department of Agriculture, Peoria, Ill., 61604 on Apr. 22, 1992, under the accession number NRRL B-18967. SEQ ID NO:2 can be isolated from the plasmid, for example, as a 4.2 kb EcoR1/Kpn1 restriction fragment. Other fragments are also useful in obtaining SEQ ID NO:2.

Additionally, the DNA sequences can be synthesized using automated DNA synthesizers, such as the ABS (Applied Biosystems, 850 Lincoln Centre Drive, Foster City, Calif. 94404) 380B DNA synthesizer. The DNA sequences can also be generated by the polymerase chain reaction (PCR) as described in U.S. Pat. No. 4,189,818, herein incorporated by reference.

Because skilled artisans will recognize that many vectors are available for expression and cloning, those expression and cloning vectors which comprise nucleic acids which encode SEQ ID NO:1 are included in the present invention. The preferred nucleic acid vectors are those which are DNA. Most preferred are recombinant DNA vectors which comprise the isolated DNA sequence which is SEQ ID NO:2. The recombinant DNA vector most preferred is plasmid pRS103.

DNA vectors which further comprise a promoter positioned to drive expression of functional HSGluR1 receptor are also provided. Preferred recombinant DNA expression vectors are those wherein the promoter functions in mammalian cells. More preferred recombinant DNA expression vectors are those wherein the promoter functions in COS-7 cells. Most preferred COS-7 DNA expression vectors further comprise SEQ ID NO:2.

Restriction fragments of these vectors are also provided. The preferred fragments are the 4.2 kb EcoR1/Kpn1 restriction fragment and the 2.8 kb EcoRI/ClaI restriction fragment of pRS103.

Plasmid pRS103 may be isolated from the deposited E. coli[<m]ed/pRS103, using an ordinary cesium chloride DNA isolation procedure. Plasmid pRS103 is readily utilized to construct expression vectors that produce HSGluR1 receptors in a variety of organisms and cell lines, including, for example, CV1 cells, COS cells, CHO cells, E. coli, Sf9 (as host for baculovirus), Pichia and Saccharomyceyes. The current literature contains techniques for constructing expression vectors and for transfecting host cells. For example, Sambrook et al., *Molecular Cloning: A Laboratory Manual* Chapters 16 and 17 (1989), explains these techniques.

The construction protocols discussed in Sambrook et al. can be followed to construct analogous vectors for other organisms merely by substituting, if necessary, the appropriate regulatory elements using techniques well known to skilled artisans. Promoters which may be used, for example, are the thymidine kinase promoter, the metallothionin promoter or various viral and immunoglobulin promoters.

The DNA compounds of the present invention also include primers or probes. Nucleic acid compounds of at least 17 base pairs which encode all or a part of SEQ ID NO:1 are included in the present invention. DNA is the preferred nucleic acid used as a probe or primer. Most preferred DNA compounds useful as probes or primers are: SEQ ID NO:3, SEQ ID NO:4 and SEQ ID NO:5. A skilled artisan would recognize the techniques associated with probes and primers as well known in the art. Any sequence of at least 17 base pairs in length of the nucleic acids of the present invention may be used to screen any other nucleic acid. For example, all or part of SEQ ID NO:3 and all or part of the reverse complement of SEQ ID NO:5 may be used to hybridize to the terminal ends of the coding sequence. Then, through PCR amplification, the full length sequence may be generated. The full length sequence can be subsequently subcloned into any vector of choice.

Alternatively, SEQ ID NO:3, SEQ ID NO:4, or SEQ ID NO:5 may be radioactively labeled at the 5' end in order to screen cDNA libraries by conventional means. Furthermore, any piece of HSGluR1 DNA which has been bound to a filter may be flooded with total mRNA transcripts, in order to then reverse-transcribe the mRNA transcripts which bind.

Primers and probes may be obtained by means well known in the art. For example, once pRS103 is isolated, restriction enzymes and subsequent gel separation may be used to isolate the fragment of choice.

Host cells which harbor the nucleic acids provided by the present invention are also provided. Oocytes, mammalian cells and E. coli cells are specifically preferred. COS-7 cells are the most preferred mammalian cells provided.

Oocytes which, in addition to harboring nucleic acids capable of expressing functional HSGluR1 receptor, further harbors nucleic acids capable of expressing functional GluR2 receptor are provided. Oocytes which, in addition to harboring nucleic acids capable of expressing functional HSGluR1 receptor, also harbors nucleic acids capable of expressing functional GluR2 receptor and also harbors nucleic acids capable of expressing functional GluR3 receptor are also provided. Most preferred oocytes of the present invention are those which harbor sense mRNA.

Host cells which are transfected with a DNA vector having a promoter positioned to drive expression of functional HSGluR1 receptor are also provided. Preferably, the DNA vector comprises SEQ ID NO:2. Preferred host cells for expression of functional HSGluR1 are mammalian cells. Preferred mammalian cells for expression of functional HSGluR1 are COS-7 cells. Specifically, COS-7 cells which have been transfected with a DNA expression vector which expresses a functional HSGluR1 receptor and which further comprise a DNA vector which encodes a functional GluR2 receptor are provided. COS-7 cells which (a) have been transfected with an DNA expression vector which expresses a functional HSGluR1 receptor, and (b) further comprise a DNA vector which encodes a functional GluR2 receptor, and (c) further comprise a DNA vector which encodes a functional GluR3 receptor are also provided. Wigler M. et al., 16 Cell 777 (1979), describe such a cotransfection procedure.

Preferred host cells also include *E. coli* cells. The more preferred *E.coli* cells are those which have been transfected with a DNA vector. Most preferred *E.coli* host cells are those which have been transfected with a DNA expression vector which comprises SEQ ID NO:2. The most preferred *E.coli* cell is one transfected with plasmid pRS/103.

Oocytes harboring foreign nucleic acids can be constructed according to the procedures described in Lübbert, et al. 84 *Proc. Mat. Acad. Sci.* 4332 (1987) and Berger, Methods in Enzymology, Vol. 152 (1987). Other host cell transfection procedures are well known in the art. Nucleic acids which encode GluR2 and GluR3 can be obtained according to Heinemann S. et al., PCT publication WO91/06648 (1992).

The present invention also provides a method for constructing a recombinant host cell capable of expressing SEQ ID NO:1, said method comprising transfecting a host cell with a recombinant DNA vector that comprises an isolated DNA sequence which encodes SEQ ID NO:1.

A preferred host cell for this method is COS-7. An especially preferred expression vector in COS-7 is one which is DNA. An especially preferred method comprises a DNA expression vector which comprises SEQ ID NO:2. Transformed host cells may be cultured under conditions well known to skilled artisans such that SEQ ID NO:1 is expressed, thus producing HSGluR1 activity in the recombinant host cell.

Therefore, also provided by the present invention is a method for expressing a gene which encodes SEQ ID NO:1 in a recombinant host cell, said method comprising culturing said transfected host cell under conditions suitable for gene expression. A preferred method utilizes mammalian cells. A most preferred method utilizes COS-7 cells. A more preferred method utilizes COS-7 cells as host cells for a recombinant DNA vector. A most preferred method utilizes COS-7 cells as host cells for a recombinant DNA vector comprising SEQ ID NO:2. Expression in host cells may be accomplished according to the procedures outlined in Sambrook et al., *Molecular Cloning: A Laboratory Manual* 16–17 (1989).

Additionally, the invention provides a method for identifying DNA homologous to a probe of the present invention, which comprises contacting the test nucleic acid with the probe under hybridizing conditions and identified as being homologous to the probe. The preferred probes for use in this method are SEQ ID NO:3, SEQ ID NO:4 or SEQ ID NO:5. Hybridization techniques are well known in the art. Sambrook et al., *Molecular Cloning: A Laboratory Manual* 11 (1989) describe such procedures.

Assays utilizing the compounds provided by the present invention are also provided. Assays provided include a method for determining whether a substance evokes a glutaminergic response, said method comprising introducing said substance and a functional compound of SEQ ID NO:1 into an acceptable medium, and subsequently monitoring glutaminergic activity by physically detectable means, and thereby identifying those substances which effect a chosen response. Other assays further comprise a functional GluR2 receptor. A preferred assay further comprises both the GluR2 and the GluR3 receptor.

Preferably, the physically detectable means is competition with radiolabeled glutamate, binding of glutaminergic ligand or generating a detectable ion flow. A preferred assay is an oocyte assay system. A most preferred oocyte assay system utilizes sense mRNA. Most preferred is an assay wherein the oocyte expression system utilizes sense mRNA.

The oocyte expression system can be constructed according to the procedure described in Lübbert, et al. 84 *Proc. Nat. Acad. Sci.* 4332 (1987) and Berger, Methods in Enzymology, Vol.152 (1987). The radiolabeled HSGluR1 competition assay may be accomplished according to Nelson, et al., 41 *Life Sciences* 1567 (1987). The assay which measures ion flow in mammalian cells may be accomplished according to Hamill O.P. et al., 391 (No. 2) Pflugers Archiv:European J. of Physiology, 85 (1981).

Skilled artisans will recognize that competition assays results are described in terms of $K_i$ values. Moreover, skilled artisans realize that desirable $K_i$ values are dependent on the selectivity of the compound tested. For example, a compound with a $K_i$ which is less than 10 nM is generally considered an excellent candidate for drug therapy. However, a compound which has a lower affinity, but is selective for the particular receptor, may be an even better candidate.

The present invention provides assays, which indicate whether a substance has either a high affinity or low affinity to HSGluR1 receptor, because skilled artisans will recognize that any information regarding binding or selectivity of a particular compound is beneficial in the pharmaceutical development of drugs.

The following are examples of the present invention:

EXAMPLE 1

Growth of *E. coli*/pRS103

A lyophilized culture of *E. coli* containing plasmid pRS103 can be obtained from the American Type Culture Collection, Rockville, Md. 20852, and inoculated into a suitable broth for the growth of *E. coli* using standard microbiological procedures.

The contents of a lyophil vial containing *E. coli*/pRS103 were transferred into 100 ml of sterile YT (tryptone-yeast extract) broth containing 100 µg/ml ampicillin in a one liter fermentation flask and shaken at 37° C. on an orbital shaker at 250–300 rpm. After the optical density (OD, measured at 600 millimicrons) had reached approximately 1–2 OD, the bacterial cells were recovered and used for the isolation of plasmid pRS103 according to the procedures detailed in J. Sambrook et al., *Molecular Cloning*, Chapter 1, (1999).

Once isolated from the bacterial cells, the plasmid DNA served as a source for the DNA encoding the human HSGluR1 receptor protein. One convenient method to remove the receptor-encoding DNA from plasmid pRS103 was to digest the plasmid with restriction enzymes EcoRI and Kpn I. These enzymes cut the plasmid at unique sites to produce a DNA fragment of approximately 4.2 kb containing the entire coding sequence of the human HSGluR1 receptor.

EXAMPLE 2

In Vitro Transcription of RNA using pRS103 as a DNA Template

RNA transcripts encoding the HSGluR1 receptor were produced by enzymatic transcription from pRS103 using an RNA polymerase which recognizes the transcription promoter contained in the plasmid adjacent to the amino terminal coding end of the receptor subunit cDNA. Plasmid pRS103 was treated with the restriction enzyme SalI which made a single cut distal to the 3' end of the cDNA insert in the circular DNA and converted the plasmid DNA into a linear form. This DNA was then incubated with T7 RNA polymerase in the presence of GppppG cap nucleotide, rATP, rCTP, rUTP and rGTP. The synthetic RNA transcript obtained was purified by passage over a Sephadex G-50 column. For a detailed description of in vitro RNA synthesis using bacteriophage RNA polymerase such as T7, see P. A. Krieg and D. A. Melton, Vol 155, *Methods in Enzymology*, Ch. 25, 1987.

EXAMPLE 3

Functional Expression of Human HSGluR1 Receptor in Xenopus Oocytes.

Oocytes suitable for injection were obtained from the adult female *Xenopus laevis* using procedures described in C. J. Marcus-Sekura and M. J. M. Hitchcock, *Methods in Enzymology*, Vol. 152 (1997). After treatment with collagenase type 1a (Sigma) at a concentration of 2 mg/ml, the defolliculated oocytes were injected essentially as described by M. J. M. Hitchcock et al., *Methods in Enzymology*, Vol. 152 Chapter 22, (1997). Subsequently, 5 ng of RNA transcript in a total volume of 50 nl, prepared as described in Example 2, were injected into each oocyte and they were then incubated in Barth's saline solution at 18° C. until needed for electrophysiological measurements.

In order to detect the presence of HSGluR1 receptor, the ability of the receptor to assemble into functional ion channels was determined by voltage recording of electrical current flowing across the oocyte membrane in response to glutamate agonists. Individual oocytes were placed in a diffusion chamber (0.5 ml vol.) through which solutions were perfused rapidly. Drugs (agonists and antagonists) were applied to the oocytes by adding them to the perfusing solutions and subsequently washing them out with control solution. The control solution contained 96 nM NaCl, 2 mM KCl, 1.8 nM CaCl2, 1 MgCl2, and 5 mM HEPES buffer, pH 7.6. After insertion of electrodes into the oocytes, voltage recordings were made using the bridge circuit of an Axoclamp 1A voltage-clamp unit. Microelectrodes were filled with 3 M CsCl. Electrophysiological recordings of the oocytes clamped at −70 mV were made at room temperature (20–25° C.), 3 days or more after injection of RNA into the oocytes. In response to perfusion of the cells with 100 $\mu$M kainic acid, an inward current across the oocyte membrane of 10–30 nano-amperes was observed. For a detailed discussion of the electrophysiology of Xenopus oocytes see N. Dascal, 22 CRC *Critical Reviews in Biochemistry*, 317 (1987). As those skilled in the art appreciate these results are indicative of a glutamate receptor.

---

We claim:
1. An isolated DNA compound encoding a glutamate receptor having a sequence as defined by SEQ ID NO:2.

* * * * *